US00PP32979P2

(12) United States Plant Patent
Griffin

(10) Patent No.: US PP32,979 P2
(45) Date of Patent: Apr. 13, 2021

(54) ***ALOE* PLANT NAMED 'SIDEWINDER'**

(50) Latin Name: ***Aloe* hybrid**
Varietal Denomination: SIDEWINDER

(71) Applicant: Altman Specialty Plants, Inc, Vista, CA (US)

(72) Inventor: Kelly Griffin, Carlsbad, CA (US)

(73) Assignee: Altman Specialty Plants Inc., Vista, CA (US)

( * ) Notice: Subject to any disclaimer, the term of this patent is extended or adjusted under 35 U.S.C. 154(b) by 0 days.

(21) Appl. No.: 16/873,344

(22) Filed: Mar. 24, 2020

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Aloe* plant named 'SIDEWINDER' is disclosed, characterized by an open star shape, white, green and pink leaves, and light red flowers. The new variety is an *Aloe*, typically produced as a garden or container plant.

2 Drawing Sheets

Latin name of the genus and species: *Aloe* hybrid.
Variety denomination: 'SIDEWINDER'.

BACKGROUND OF THE INVENTION

The new cultivar is a product of a planned breeding program. The seed parent is the unpatented *Aloe* 'Sunrise'. The pollen parent is the unpatented *Aloe* 'Delta Lights' x 'Neon Lights'. The crossing was made in December 2015 at a commercial greenhouse in Vista, Calif. 'SIDEWINDER' was found and selected by the inventor in May 2017 at the same greenhouse in Vista, Calif.

Asexual reproduction of the new cultivar 'SIDEWINDER' was first performed by tissue culture at a commercial laboratory in Vista, Calif. in July 2017. 'SIDEWINDER' has since produced several generations and has shown that the unique features of this cultivar are stable and reproduced true to type.

SUMMARY OF THE INVENTION

The cultivar 'SIDEWINDER' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SIDEWINDER'. These characteristics in combination distinguish 'SIDEWINDER' as a new and distinct *Aloe* cultivar:

1. Open star shape.
2. White, green and pink leaves with raised barred protrusions.
3. Light red flowers.
4. Table top size *Aloe*, maturing to 8" across.

PARENTAL COMPARISON

Plants of the new cultivar 'SIDEWINDER' are similar to the seed parent in most horticultural characteristics. However, plants of the new variety differ from the seed parent in the following:

1. The new variety has a more compact, upright rosette than the seed parent.
2. The new variety has smoother leaf edges than the seed parent.
3. The seed parent does not have the barred leaf pattern found on the new variety.

Plants of the new cultivar 'SIDEWINDER' are similar to the pollen parent in most horticultural characteristics. However, plants of the new variety differ in the following:

1. The pollen parent has sharper and larger marginal serrations.
2. The pollen parent does not exhibit the distinct star shaped plant.

COMMERCIAL COMPARISON

'SIDEWINDER' can be compared to the unpatented commercial variety *Aloe* 'White Lightning'. The two *Aloe* varieties are similar in most horticultural characteristics; however, the new variety differs in the following:

1. The new variety is a larger, more open plant than this comparator.
2. This comparator has sharper and larger marginal serrations.
3. The new variety has a cleaner, more uniform growth habit than this comparator.

BRIEF DESCRIPTION OF THE PHOTOGRAPHS

Figure 1:
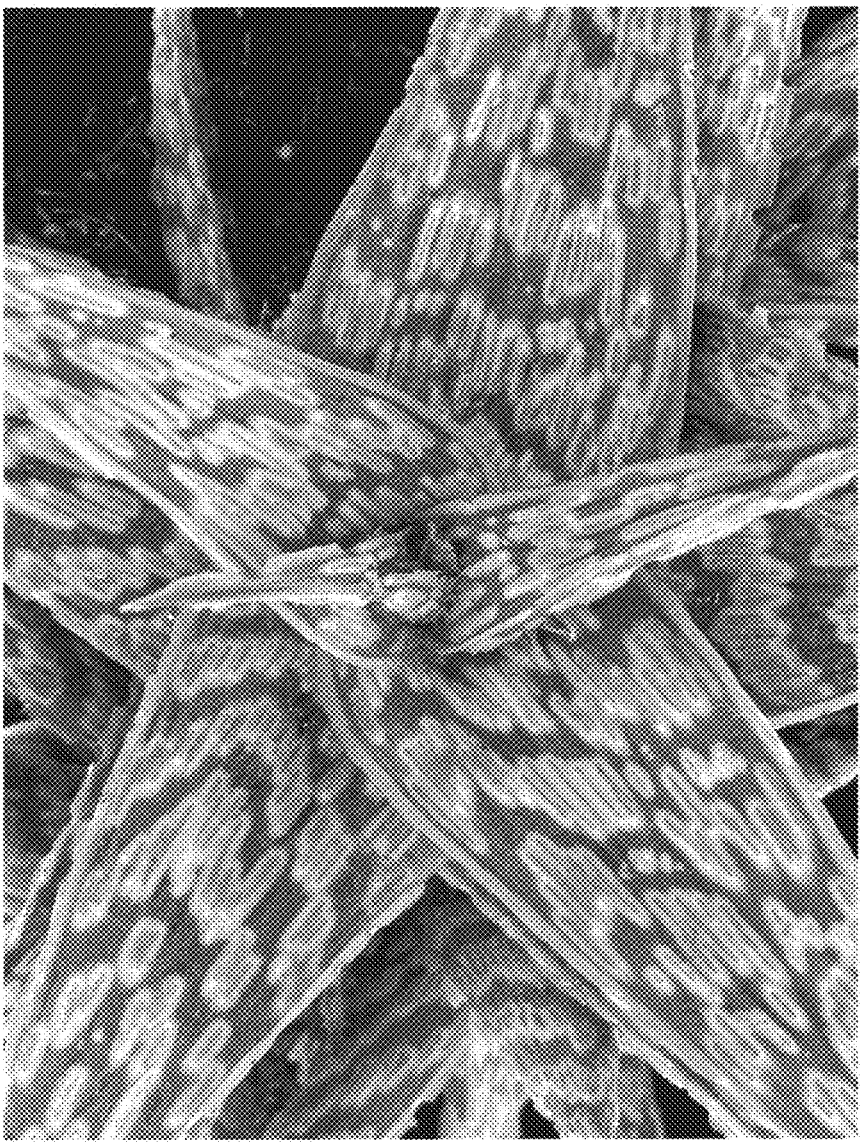

The accompanying photographs in FIG. 1 illustrate in full color a typical plant of 'SIDEWINDER' grown in a greenhouse in Vista, Calif. This plant is approximately 24 months old, shown in a 1-gallon container.

Figure 2:
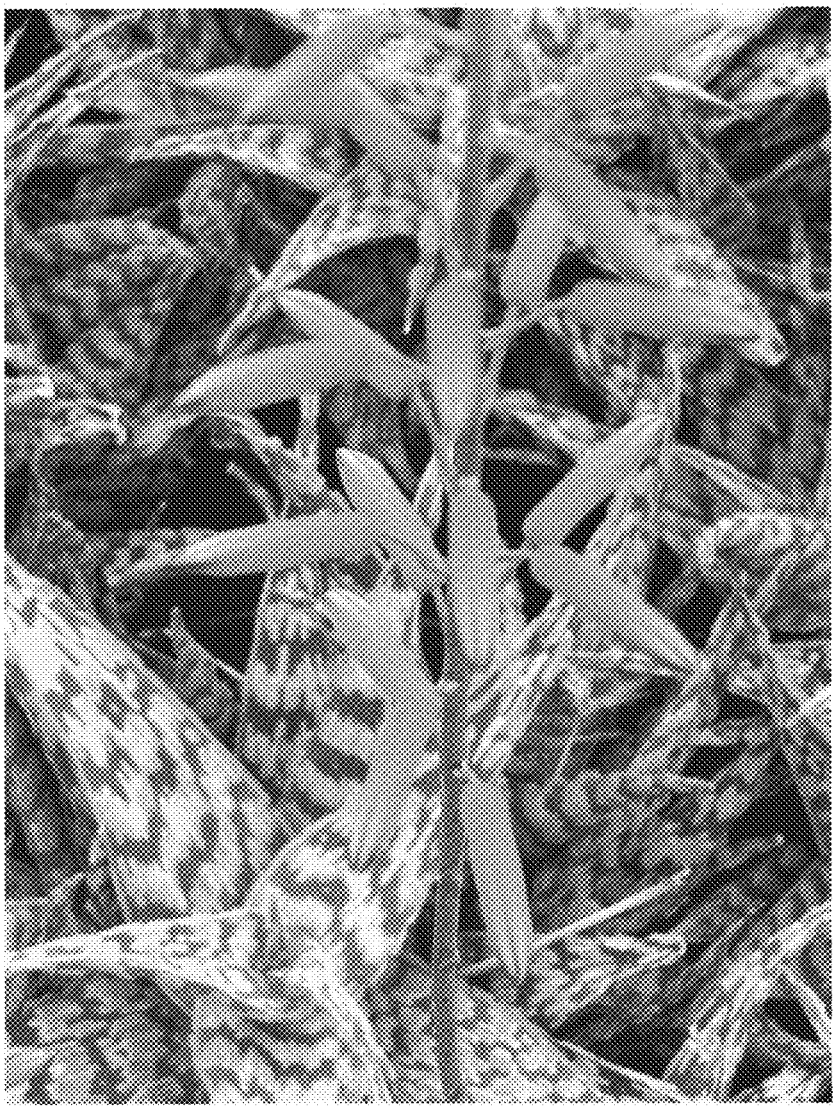

FIG. 2 illustrates in the florescence of the new variety 'SIDEWINDER'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'SIDEWINDER' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'SIDEWINDER'.

Age of the plant described: 2 years.

PROPAGATION

Time to initiate roots: Approximately 25 days at 22° C.

Root description: Fibrous. Brown, not accurately measured with The R.H.S. Chart.

Propagation method: Tissue culture.

PLANT

Growth habit: Upright rosette, offsetting to form clumps with time.

Container size: 6 inches.

Height: Approximately 16 cm to top of highest leaf. Approximately 35 cm to top of highest inflorescence.

Plant spread: Approximately 25 cm.

Growth rate: Moderate.

Branching characteristics: Offsets from base.

FOLIAGE

Leaf:

*Arrangement*.—Rosette.

*Average length*.—Average 14-16 cm.

*Average width*.—Average 3-4 cm.

*Shape of blade*.—Lanceolate, slightly deltoid.

*Apex*.—Acuminate.

*Base*.—Clasping.

*Margin*.—Bars and raised ribs.

*Texture of top surface*.—Bars and ribs.

*Texture of bottom surface*.—Bars and ribs.

*Quantity of leaves per plant*.—Average 10.

*Color*.—Young foliage upper side: Near RHS Green 136C, densely covered in elongated bars, about 1 to 2 mm wide and 3 to 6 mm long. Bars colored near Orange-Red 35A and 35B. Margin colored near Orange 35B. Young foliage under side: Near RHS Green 136C, sparsely covered in elongated bars, about 1 to 2 mm wide and 3 to 6 mm long. Bars colored near Orange-Red 35B. Margin colored near Orange 35B. Mature foliage upper side: Near RHS Green 136C, densely covered in elongated bars, about 1 to 2 mm wide and 3 to 6 mm long. Bars colored near Orange-Red 35A and 35B. Margin colored near Orange 35C. Mature foliage under side: Near RHS Green 136C, sparsely covered in elongated bars, about 1 to 2 mm wide and 3 to 6 mm long. Bars colored near Orange-Red 35C. Margin colored near Orange 35C.

*Venation*.—Linear. Color: Indistinguishable from leaf blade.

FLOWER

Natural flowering season: Rebloomer, three to four times a year.

Inflorescence type and habit: Panicle, seldom branched.

Rate of flower opening: Moderate, successive.

Flower longevity on plant: 1.5 months.

Quantity of flowers: 10 to 20.

Total inflorescence size:

*Height*.—Approximately 30 cm.

*Width*.—Approximately 8 cm.

Corolla:

*Arrangement*.—Perianth cylindrical/corolla small and reflexed.

*Length*.—Approximately 2.5 cm.

*Width*.—Approximately 1 cm at widest point.

*Tepals*.—Typically fused, the most mature flowers split at apex into 6 tepals/lobes. Unfused portion about 3 mm long and 3 mm wide.

*Color*.—Tepals: When opening: Outer surface: Near RHS Red 48A. Inner surface: Near RHS Yellow-Orange 18D. Fully opened: Outer surface: Near RHS Red 48A. Inner surface: Near RHS Yellow-Orange 18D.

Bud:

*Shape*.—Cylindrical.

*Length*.—Approximately 2.5 cm.

*Diameter*.—Approximately 0.5 cm.

*Color*.—Near RHS Red 48A.

Peduncle:

*Length*.—Approximately 1 cm.

*Width*.—About 6 mm.

*Color*.—Near Greyed-Purple N187C+.

Pedicels:

*Length*.—Approximately 1 cm.

*Width*.—2 mm.

*Aspect*.—Lateral.

*Color*.—Near RHS Red 39B.

Fragrance: None.

REPRODUCTIVE ORGANS

Stamens:

*Number*.—6.

*Filament length*.—Approximately 2.5 cm.

*Filament color*.—Near RHS White 155D.

*Anther length*.—0.25 cm.

*Anther color*.—Near Yellow 7A

*Anther shape*.—Oval.

*Pollen color*.—Near Yellow 7A.

Pistil:

*Number*.—1.

*Length*.—Approximately 3 cm.

*Style color*.—Near RHS White 155D.

*Stigma*.—Shape: Rounded. Color: Near RHS White 155D. Ovary color: Near RHS Greyed-Green 193C.

OTHER CHARACTERISTICS

Seeds and fruits: Pods about 10 mm long and 5 mm wide, colored near Green 137D when immature, ripening to Grey-Brown N199D. Seed dust like, colored near Grey-Brown 199C.

Temperature tolerance: Tolerates temperatures from approximately 0° to at least 35° C.

Disease/pest resistance: Shows mite resistance and black spot resistance (pathogen unconfirmed).

What is claimed is:

1. A new and distinct cultivar of *Aloe* plant named 'SIDEWINDER' as herein illustrated and described.

* * * * *